United States Patent [19]
Thym et al.

[11] Patent Number: 6,036,919
[45] Date of Patent: Mar. 14, 2000

[54] DIAGNOSTIC TEST CARRIER WITH MULTILAYER FIELD

[75] Inventors: Detlef Thym, Mannheim; Wofgang-Reinhold Knappe, Ludwigshafen; Rudolf Pachl, Ellerstadt; Hartmut Merdes, Heidelberg; Robert Lorenz, Worms, all of Germany

[73] Assignee: Roche Diagnostic GmbH, Mannheim, Germany

[21] Appl. No.: 08/897,513

[22] Filed: Jul. 21, 1997

[30] Foreign Application Priority Data

Jul. 23, 1996 [DE] Germany .............. 196 29 656

[51] Int. Cl.⁷ .................................. G01N 33/49
[52] U.S. Cl. .................. 422/58; 422/61; 436/66; 436/164; 436/169; 436/170; 436/175
[58] Field of Search ................ 422/56, 58, 61; 436/164, 166, 169–170, 175, 66–68

[56] References Cited

U.S. PATENT DOCUMENTS

| | | | |
|---|---|---|---|
| 3,630,957 | 12/1971 | Rey et al. | 252/408 |
| 4,477,575 | 10/1984 | Vogel et al. | 436/170 |
| 4,816,224 | 3/1989 | Vogel et al. | 422/55 |
| 4,987,085 | 1/1991 | Allen et al. | 422/58 |
| 5,169,787 | 12/1992 | Knappe et al. | 422/58 |
| 5,215,886 | 6/1993 | Patel et al. | 422/56 |
| 5,260,195 | 11/1993 | Azhar et al. | 422/56 |
| 5,262,067 | 11/1993 | Wilk et al. | 422/56 |
| 5,290,515 | 3/1994 | Plesch et al. . | |
| 5,536,470 | 7/1996 | Frey et al. . | |

FOREIGN PATENT DOCUMENTS 1177374  11/1984  Canada .
0 217 246  4/1987  European Pat. Off. .

OTHER PUBLICATIONS

Derwent Patent Abstract for EP–45476B, Derwent WPI No. 82–12079E, Jul. 1982.

Derwent Patent Abstract for EP–302287, Derwent WPI No. 89–040472, Jun. 1989.

*Primary Examiner*—Lyle A. Alexander
*Attorney, Agent, or Firm*—Nikaido Marmelstein Murray & Oram LLP

[57] ABSTRACT

The present invention concerns a diagnostic test carrier for the determination of an analyte from whole blood with the aid of a reagent system contained in the carrier which includes a colour forming reagent with a test field which has a sample application side onto which the blood sample is applied and a detection side on which an optically detectable change takes place as a result of the reaction of analyte with the reagent system and which is constructed in such a way that erythrocytes present in the sample do not reach the detection side, which is characterized in that the test field comprises a transparent foil onto which a first and a second film layer are applied on top of one another and wherein the first layer located on the transparent foil scatters light considerably less in a wet state than the overlying second layer and wherein the side of the foil on which the first layer is applied which is opposite to the foil side is the detection side and the side of the second layer which is opposite to the side with which the second layer rests on the first is the sample application side. In addition the invention concerns a method for the determination of an analyte from whole blood with the aid of a diagnostic test carrier according to the invention.

27 Claims, 7 Drawing Sheets

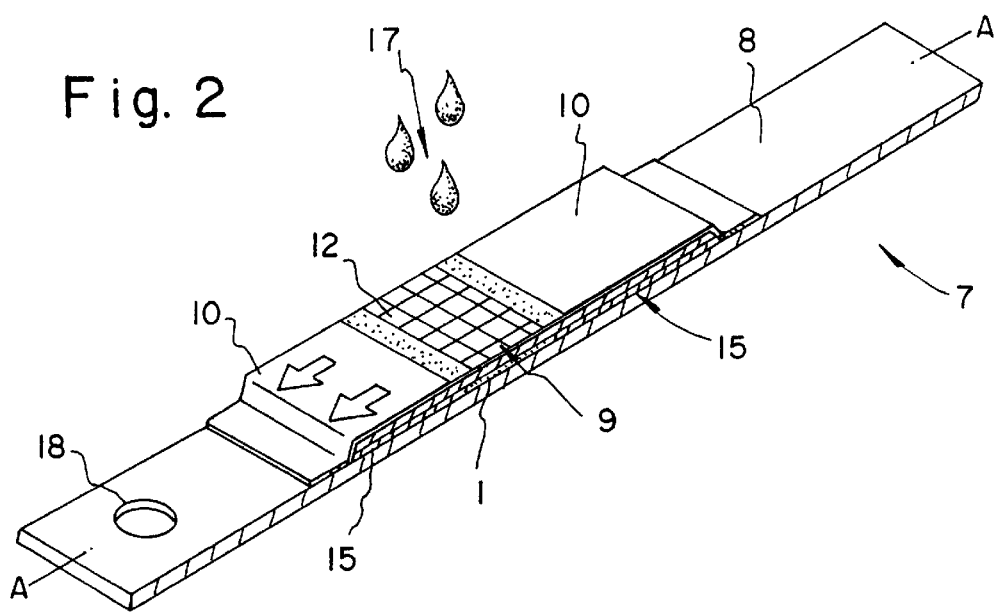
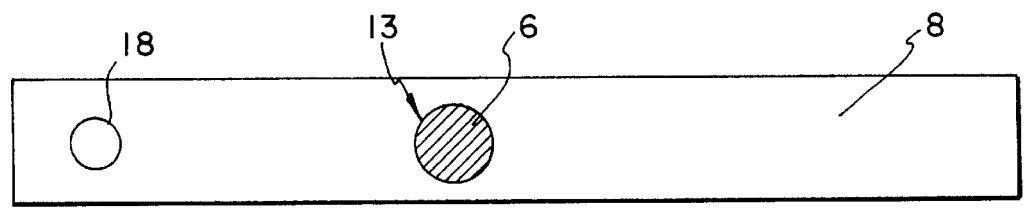
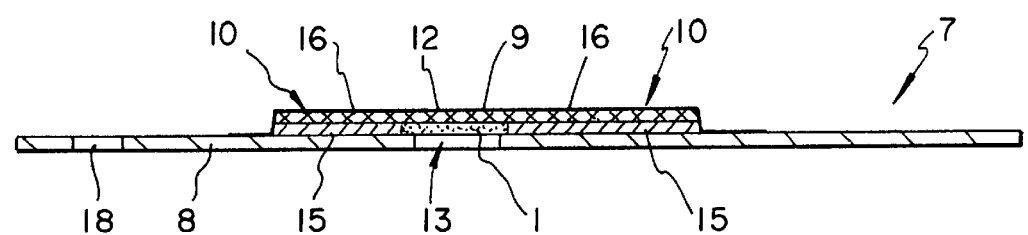

DIAGNOSTIC TEST CARRIER WITH MULTILAYER FIELD

The invention concerns a diagnostic test carrier to determine an analyte from whole blood using a reagent system contained in the test carrier which includes a colour generating reagent with a test field which comprises a sample application site onto which the blood sample is introduced and a detection side on which, as a result of the reaction of the analyte with the reagent system, an optically detectable change takes place and which is designed in such a way that erythrocytes present in the sample do not reach the detection site. In addition the invention concerns a method for the determination of an analyte from whole blood with the aid of a diagnostic test carrier according to the invention.

So-called carrier-bound tests are often used for the qualitative or quantitative analytical determination of components in body fluids in particular in blood. In these the reagents are present on or in appropriate layers of a solid test carrier which is contacted with the sample. The reaction of the liquid sample and reagents leads to a detectable signal in particular to a change in colour which can be analyzed visually or with the aid of an instrument, usually by reflection photometry.

Test carriers are frequently in the form of test strips which are composed essentially of an elongate supporting layer made of plastic material and test fields mounted thereon composed of one or several detection layers. However, test carriers are also known which are shaped as small quadrangular or rectangular foils.

Carrier-bound tests are in particular distinguished by their easy handling. Thus it is even more regrettable that in most previously known test carriers the sample liquid blood cannot be used directly in the form of whole blood. On the contrary it is necessary to separate red blood cells (erythrocytes) in order to obtain colourless plasma or serum. This is usually achieved by centrifugation. However, this requires an additional handling step which requires a relatively large amount of blood and complicated apparatus.

Many attempts have therefore been made to provide test carriers which enable analytical determinations to be carried out directly from blood. One can differentiate between two fundamentally different solutions.

In the first approach the change in colour is evaluated visually or by means of an apparatus on the same side of the test field to which the sample is also applied. In this case the structure of the test field is such that the analyte from the sample reaches the reagents through the surface of the test field whereas erythrocytes are held back. After a defined time period the blood sample is wiped or washed away from the surface of the test field and the change in colour is observed. Examples of such test carriers are described in U.S. Pat No. 3,630,957 and in EP-A-0 217 246.

In the second approach the sample is applied to one side of the test field (sample application side) and the change in colour is registered on the other side (detection side). A major advantage of this procedure is that blood does not have to be wiped or washed away. Such test carriers are therefore also referred to as non-wipe test carriers.

Omission of wiping not only eliminates one tedious handling step but also a possible source of errors which can result when the time at which the blood should be wiped away is not exactly adhered to. On the other hand this approach is particularly difficult to achieve. An erythrocyte filter is required which on the one hand reliably retains intensively colouring components of blood but on the other hand allows the analyte to pass completely and rapidly enough. It has proven to be extremely difficult to find a test field structure that fulfils these requirements.

It is known from EP-A-0 045 476 that glass fibres are used to isolate serum or plasma on a test carrier. This solution can be used universally but it is necessary to mount the glass fibre layers onto the test carrier in a suitable way. This results in a relatively complicated construction of the test carrier and the production process is complicated. In addition the glass fibre layer absorbs liquid which is then not available for the detection layer. This means that relatively high sample volumes are necessary.

A test field is shown in EP-A-0 302 287 which has a layered structure that is manufactured by liquid layering a detection layer containing the colour forming reagent on a base layer that faces the sample application side. The base layer contains a polymeric film former, kieselguhr and a pigment. The detection layer contains a polymeric film former which partially penetrates into the base layer during the liquid coating and forms a transition zone in which erythrocytes are retained. As can be seen from the examples the layer containing pigment is, however, up to 10-times thicker than the detection layer. This has a considerable impact on the volume requirements of such a test field. Since only the transition zone between the layer containing pigment and the detection layer serves as an erythrocyte retention zone, a relatively large volume (of the layer containing pigment) has to be filled with liquid before the detection layer is filled with liquid.

Since none of the previous implementations of a NW test carrier with erythrocyte separation exhibits satisfying properties in every respect, the separation of erythrocytes was completely omitted in a commercially available embodiment of such a test carrier and interference by the strong red colouration was compensated by the measuring technique by measuring at two different wavelengths. This considerably complicates the instrumental evaluation and the change in colour cannot be monitored visually.

The object of the invention is to provide a test carrier that can easily be manufactured and with which an analyte can be easily and rapidly determined from whole blood. This determination should only require the smallest possible volume of blood but nevertheless be haematocrit-independent. A simple determination should include the possibility of visually assessing the analyte concentration.

This object is achieved by the invention characterized in more detail in the patent claims.

The subject matter of the invention is a diagnostic test carrier for the determination of an analyte from whole blood with the aid of a reagent system contained in a test carrier which includes a colour forming reagent. The test carrier contains a test field which has a sample application side to which the blood sample is applied and in addition a detection side on which an optically detectable change takes place as a result of the reaction of analyte with the reagent system. Erythrocytes present in the blood do not reach the detection side. According to the invention the test field comprises a transparent foil onto which a first and a second film layer are applied resting on top of one another in this order. It is important that the first layer located on the transparent foil scatters light considerably less than the overlying second layer. The non-coated side of the transparent foil is referred to as the detection side and the side of the second layer which is opposite to the side with which the second layer rests on the first is referred to as the sample application side.

In addition the invention concerns a method for the determination of an analyte from whole blood with the aid of a diagnostic test carrier according to the invention. For this blood is applied to the sample application side of the test field and the detection side is observed for change in colour, the intensity of the colour formation being a measure of the amount of analyte in the examined blood sample.

The film layers of the diagnostic test carrier according to the invention are produced from dispersions or emulsions of polymeric film formers. Dispersion film formers contain microscopic polymer particles which are insoluble in the carrier liquid (usually water) and are finely dispersed in the carrier liquid. If the liquid is removed by evaporation during film formation then the particles come closer and finely touch one another. The large forces which occur in this process and the gain in surface energy which accompanies the film formation results in the particles growing into a substantially closed film layer. Alternatively it is also possible to use an emulsion of the film former in which this is dissolved in a solvent. The dissolved polymer is emulsified in a carrier liquid which is immiscible with the solvent.

Polyvinyl esters, polyvinyl acetates, polyacrylic esters, polymethacrylic acid, polyvinyl amides, polyamides and polystyrene are particularly suitable as polymers for such film formers. In addition to homopolymers mixed polymerizates are also suitable such as of butadiene, styrene or maleic acid ester.

The two so-called film layers are located on a transparent foil in the test field of the diagnostic test carrier according to the invention. For this those plastic foils come into consideration which are impermeable to liquid. Polycarbonate foil has proven to be particularly suitable.

The two film layers can be produced from coating compounds which contain the same polymeric film formers or they can be produced from coating compounds which contain different polymeric film formers.

Whereas the first layer contains a swelling agent and optionally a weakly light scattering filler, the second layer requires a swelling agent and in any case at least one pigment that scatters light strongly. In addition the second layer can also contain non-porous fillers as well as porous fillers such as kieselguhr in small amounts without becoming permeable for erythrocytes. The ratio by weight of pigment to kieselguhr should be at least 2:1.

By adding a swelling agent that swells well (i.e. a substance which increases its volume when it takes up water) one does not only obtain layers which can be penetrated relatively rapidly by sample liquid but have good erythrocyte and additionally also blood pigment separation properties despite this opening effect of the swelling agent. The swelling properties should be so good that for a test in which the rate of colour formation—such as for example of a glucose test reaction—is mainly dependent on the penetration of the sample liquid through the layer, the optically detectable reaction is measurable after a maximum of one minute. Especially suitable swelling agents have proven to be methyl vinyl ether maleic acid anhydride copolymer, xanthan gum and methyl vinyl ether maleic acid copolymer.

Kieselguhr is also denoted diatomaceous earth. These are deposits that have formed from silicic acid backbones of the diatomaceous types which are mined in various places. The kieselguhr that is preferably used has an average particle diameter of 5–15 $\mu$m, these values being determined with a type 715 laser granulometer which is sold by the Pabisch Company, Munich, Germany.

The amount of the strongly light-scattering pigment in the second layer is at least 25% by weight relative to the dry ready-to-use double layer of the test field. Since the weakly light-scattering fillers and the strongly light-scattering pigments are essential for the optical properties of the film layers, the first and the second film layer have different fillers and pigments.

The first film layer should either contain no fillers or those fillers whose refractive index is near to the refractive index of water. Silicone dioxide, silicates and aluminium silicates have proven to be particularly suitable for this. A sodium aluminium silicate with the commercial name Traspafill® is particularly preferred. It has an average composition of 66% by weight $SiO_2$, 26% by weight $Al_2O_3$, 7% by weight $Na_2O$ and 1% by weight $SO_3$. The average granulate size of particularly preferred primary particles is about 0.06 $\mu$m.

According to the invention the second layer should scatter light very strongly. Ideally the refractive index of the pigments in the second film layer should be at least 2.5. Hence titanium dioxide is preferably used. Particles with an average diameter of about 0.2 to 0.8 $\mu$m have proven to be particularly advantageous. Easily processable titanium dioxide types in the anatase modification are quite especially preferred.

Reagent systems for the detection of particular analytes by colour formation are known to a person skilled in the art. It is possible that all components of the reagent system are located in one film layer. However, it is also possible that the components of the reagent system are divided among both film layers. The colour generating reagent system is advantageously located at least partially in the first film layer.

Colour formation within the scope of the present invention is not only understood as a transition from white to coloured but also as any change in colour, such changes of colour of course being particularly preferred which are associated with the largest possible shift of the maximum absorption wavelength ($\lambda_{max}$).

In order to optimize the test field in the diagnostic test carrier according to the invention it has proven to be particularly advantageous when both film layers do contain a non-haemolyzing wetting agent. Neutral i.e. non-charged wetting agents are particularly preferred for this. N-octanoyl-N-methyl glucamide is most particularly preferred.

In order to produce a test field of a diagnostic test carrier according to the invention the respective film layers are each produced successively from a homogeneous dispersion of the said components. For this the transparent foil is used as a base to form the coating compound for the first film layer. After the coating compound for the first film layer has been applied with a particular layer thickness, the layer is dried. Afterwards the coating compound for the second layer is applied to this layer also with a thin layer thickness and dried. After the drying the thickness of the first and second film layer should be together no more than 0.20 mm, preferably no more than 0.12 mm particularly preferably no more than 0.08 mm. The dry second film layer is preferably about 2 to 5-times thicker than the first.

The test field produced in this manner can be mounted on a supporting layer for better handling, those materials coming into consideration for such a layer which do not take up the liquid to be examined. These are so-called non-absorptive materials, plastic foils for example made of polystyrene, polyvinyl chloride, polyester, polycarbonate or polyamide being particularly preferred. However, it is also possible to impregnate absorptive materials such as wood, paper or cardboard with water-repellent agents or to coat them with a water-resistant film in which case silicones or hard fats can be used as a hydrophobing agent and nitrocellulose or cellulose acetate can be used as film formers. Metal foils or glass are suitable as further supporting materials.

In order to determine the analyte to be detected in the sample liquid which although in the present case is preferably whole blood, samples derived from blood such as plasma or serum and also other aqueous liquids can of course also be examined, it is necessary that in the test carrier according to the invention the detection side of the test field which is to be observed and measured for colour formation should be visible through the supporting layer. This can be achieved by a transparent supporting layer. However, it is also possible that the supporting layer has a perforation which is covered by the detection side of the test field. The detection side is then visible through the perforation. In a preferred embodiment of the diagnostic test carrier according to the invention there is a hole in the supporting layer below the detection side of the test field through which the detection side of the test field can be observed. The hole has a somewhat smaller diameter than the smallest linear dimension of the test field so that the test field outside the hole rests on the supporting layer and can be attached there.

Due to the construction of the test field in particular the property of the two film layers not to allow erythrocytes to penetrate through to the detection side, only very small volumes are required to determine an analyte. When the test field has a size of 5×6 mm, 3 $\mu$l whole blood are for example adequate to determine glucose in this liquid. In order to reliably work with larger sample volumes of about 15–20 $\mu$l and to avoid liquid from leaking out of the test carrier it has proven to be particularly suitable to incorporate the test field into a diagnostic test carrier according to the invention in which this test carrier comprises a supporting layer with a test field arranged thereon and the test field is covered by a network which is larger than the test field and which is attached to the supporting layer outside the test field. The network of such a particularly preferred diagnostic test carrier according to the invention is hydrophilic but alone it is not capillary active. An inert cover made of material that is impermeable to sample liquid is arranged over those areas of the network which extend beyond the test field, i.e. the areas of the network which do not rest on the test field, in such a way that an area remains free for sample application in the region of the network which is located above the test field.

The network of this particularly preferred diagnostic test carrier according to the invention should itself not be capillary active or absorptive so that the sample liquid is available as completely as possible for the test field. Those networks have proven to be suitable which enable water to rise in the network by less than 2 mm when it is immersed vertically in water. Coarse-meshed monofilament fabrics which are hydrophilic are preferably used as the network. For this the fabric material can itself be hydrophilic or it can be made hydrophilic by for example treatment with a wetting agent. Polyester is particularly preferably used as a net material in which case the net made out of this material is then used after treatment with a wetting agent.

The thickness of the network must be such that the cover which rests on it and the layer below it are at such a distance from one another that remaining liquid is sucked over the saturated test field and the filled meshes of the network by capillary force into the area under the cover and is conducted away from the sample application site. As a rule a network thickness of 50 to 400 $\mu$m is advantageous for this.

The net must have an adequately large mesh width so that liquid can pass through the net onto the test field. The nature of the network is such that liquid is not spread horizontally in the net over the net surface but it flows vertically through the net onto the test field.

In the particularly preferred diagnostic test carrier according to the invention previously described the network which covers the test field is larger than the underlying test field. The part of the network which extends beyond the test field is fixed to the supporting layer. The attachment can be achieved by methods known to a person skilled in the area of test carrier technology. For example it can be attached by hot-setting adhesive or hardening cold-setting adhesive. Double-sided adhesive strips have also proven advantageous. However, in all cases it is important that the attachment of the network to the supporting layer is such that a capillary active liquid transport is possible from the test field into that part of the network which is attached to the supporting layer. This capillary active liquid transport must in particular be possible when the test field is saturated with liquid. Adhesive tapes made of natural or synthetic rubber have proven to be particularly suitable for the processing. It is quite especially advantageous when the agent that serves to attach the network to the supporting layer has about the same thickness as the test field. It then serves more or less as a spacer in order to hold the network overall in a continuous plane also outside the area of the test field.

An inert cover made of sample-impermeable, as a rule water-impermeable and non-absorptive material, is placed over the network of the particularly preferred diagnostic test carrier of the invention in such a way that the region of the network outside the test field is covered. Ideally the cover also protrudes a little beyond the region of the test field. However, in any case a considerable part of the network that covers the test field remains free. This free part of the network is denoted sample application site.

Plastic foils have proven to be particularly advantageous as a cover. If the cover and network have different colours for example white and yellow or white and red it is possible in this way to mark the site very well where the sample liquid to be examined should be applied.

With for example one or several printed arrows on the cover it can be also made clear in which direction i.e. with which end a diagnostic test carrier according to the invention should be placed or inserted into a measuring instrument.

A sample application site can be achieved particularly simply by a cover with the aid of two tape-like plastic foils which leave a tape-like zone of the network that covers the test field free. The foils used for the cover are attached to the network and optionally to the supporting layer. Hot melt adhesives or adhesive tapes are suitable for such an attachment if the foils are not themselves adhesive. However, in any case care must be taken that a capillary gap formed by the network remains under the cover in which excess sample liquid can be taken up from a test field saturated with liquid. The sample application site is preferably located above the perforation in the supporting layer through which signal formation can be observed in the test field.

In order to carry out a method for the determination of an analyte from whole blood with the aid of a diagnostic test carrier according to the invention blood is applied to the sample application side of the test field and the detection side is observed for colour formation. A frequent cause for false measuring values in diabetes monitoring i.e. the regular control of the blood of diabetics for their content of glucose, has up to now been sample volumes that are too small. In the case of the diagnostic test carrier according to the invention with a test field size of about 5×6 mm, 3 $\mu$l whole blood is already sufficient to carry out a visual evaluation of the examination result. Due to the fact that the second film layer of the test field is highly light scattering, the first layer in contrast being weakly light scattering, colour that forms is observed with relatively high brilliancy and colour intensity from the detection side. This enables exact determinations despite the small amounts of analyte caused by the small sample volume.

It is of course also possible to determine an analyte from whole blood with the aid of a diagnostic test carrier by an instrument. In order to achieve quantitative results that are as accurate as possible such a method is also advisable. For this the reflectance of the detection site is preferably observed continuously or at intervals for a change in colour. Reflectance measurements of the detection side of the test field are carried out in the form of a measurement series. When the difference between successive measurements falls once or several times below a certain value the measurement is terminated optionally after an additional defined reaction time. The last reflectance value of the measurement series is then used to mathematically evaluate the analyte concentration.

Since this method uses an exact criterium to terminate the measurement series and does not need the time point of sample application, the sample can also be applied outside the measuring instrument. In this case it is sufficient to insert the strip into the instrument at any desired time point after sample application within a maximum allowed period.

In the present case the method of determination is uninfluenced in the range of haematocrit values from 20 to more than 60% and can therefore be denoted haematocrit-independent when the determination is carried out using an instrument according to the above-mentioned procedure. One has to wait 2–3 minutes for visual determination before a haematocrit-independent value can be read.

BRIEF DESCRIPTION OF THE DRAWINGS

The invention is shown schematically in FIGS. 1–9.

FIG. 2 shows a perspective view of a particularly preferred diagnostic test carrier according to the invention.

FIG. 3 shows a top view of the underside of a diagnostic test carrier according to the invention according to FIG. 2.

FIG. 4 shows a cross-section along A—A through a diagnostic test carrier according to the invention according to FIG. 2.

Figure 1:
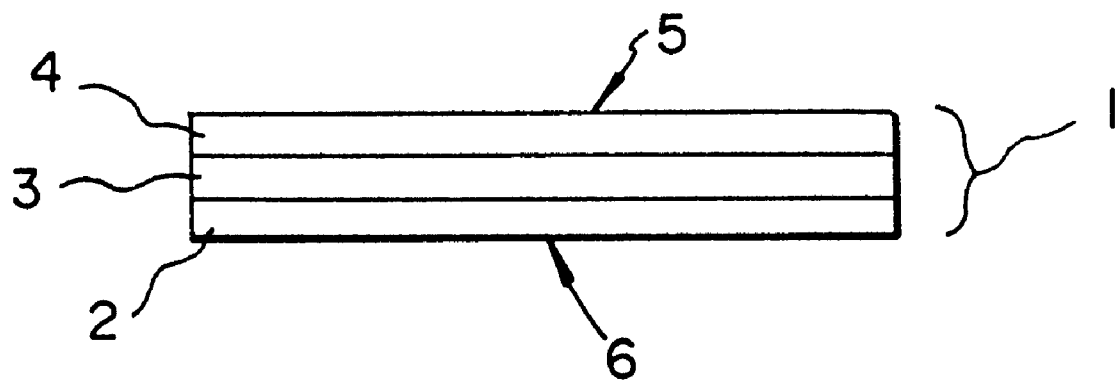
FIG. 1 shows a cross-section through the test field of a diagnostic test carrier according to the invention.

The reference numerals used in the Figures have the following meanings.

1 test field
2 transparent foil
3 first layer
4 second layer
5 sample application side
6 detection side
7 diagnostic test carrier
8 supporting layer
9 network
10 cover
11 region of the network that extends beyond the test field
12 sample application site
13 perforation
14 adhesive tape for the test field
15 spacer
16 capillary active gap
17 sample liquid
18 positioning hole The cross-section through the test field (1) shown in FIG. 1 of a diagnostic test carrier according to the invention shows the transparent foil (2) on which the first film layer (3) is applied. The first film layer (3) is covered by the second film layer (4). Manufacturing the test field (1) of the test carrier according to the invention i.e. coating the transparent foil (2) with a wet coating compound for the first film layer (3) and subsequently coating the dried first film layer (3) with a wet coating compound for the second film layer (4) results in a complete planar attachment of the layers with each other and of the first film layer (3) on the transparent foil (2). Blood which is to be examined for its contents is applied to the sample application side (5) of the test field (1) of the test carrier according to the invention. When analyte is present in the sample it is possible to observe a colour formation from the detection side (6) of the test field (1) of the test carrier according to the invention, the intensity of which depends on the amount of analyte in the sample.

The particularly preferred diagnostic test carrier (7) according to the invention shown in perspective in FIG. 2 and in cross-section in FIG. 4 is in the form of a test strip. On a supporting layer (8) there is located a test field (1) which is covered by a larger network (9). The network (9) is attached to the supporting layer (8) next to the test field (1) by means of spacers (15). These spacers (15) can be hot-melt adhesive areas or double-sided adhesive tapes which fix the network (9) onto the supporting layer (8). Ideally the spacers (15) have approximately the same thickness as the test field (1). The layers serving as a cover (10) are attached to the supporting layer (8) and the network (9). They are arranged such that they cover the region of the network (9) which extends beyond the test field (1). The covers (10) also extend slightly beyond the test field (1). However, they leave most of that part of the network (9) free which covers the test field (1). This area represents the sample application site (12). The sample liquid (17) to be examined is applied to this. The positioning hole (18) enables the test strip to be held at an exact predetermined position of the apparatus in the case of measurement by an apparatus such as by reflection photometry. This can for example be achieved by a pin which extends into the positioning hole (18) and thus holds the test carrier (7) at a predetermined position. The left cover (10) contains printed arrows which show the user which end of the test carrier (7) should be placed or inserted into a measuring instrument.

Figure 5:
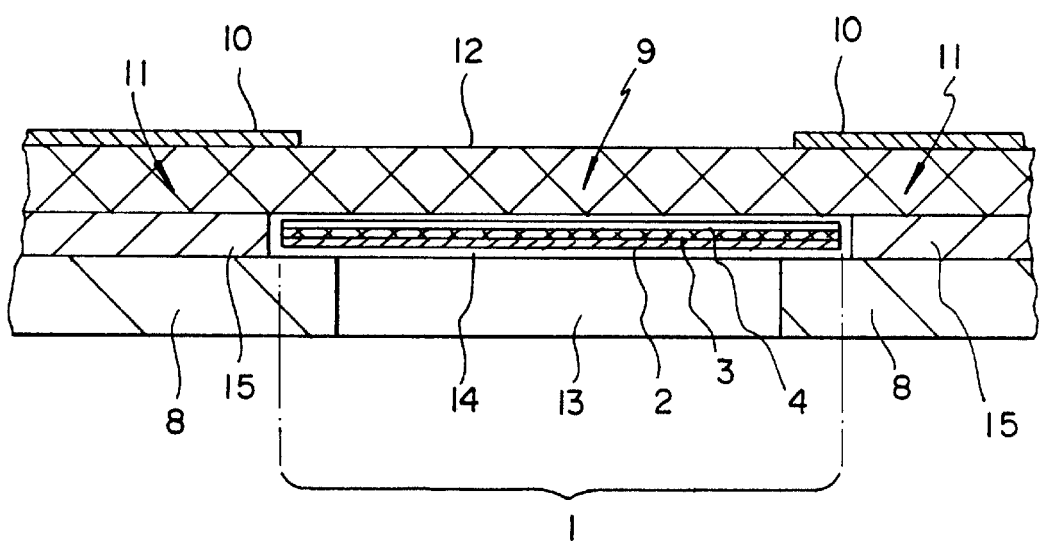
FIG. 5 shows an enlargement of part of the cross-section of FIG. 4.

FIG. 5 shows an enlarged cross-section through a particularly preferred diagnostic test carrier according to the invention as shown in FIGS. 2 and 4. This Figure is intended to elucidate how a method for the determination of an analyte in a liquid sample, for example glucose in whole blood, proceeds. For such a determination blood is applied to the sample application site (12) of the network (9). The liquid penetrates vertically through the network (9) onto the test field (1). In the case of blood as the sample liquid erythrocytes are retained there whereas plasma and serum reaches the layers (3, 4) of the test field (1). If sufficient sample liquid in the form of whole blood has been applied, plasma or serum spreads in the test field (1) in the first and second film layer (3,4) over the entire area of the test field (1). If the liquid volume is very small the test field (1) may even suck dry the overlying network (9) since the network (9) is not itself capillary active. In the case of medium to large liquid volumes the void spaces of the network (9) over the test field (1) fill first and subsequently the capillary voids under the covers (10). For these capillary voids to function properly it is necessary that the covers (10) overlap at least slightly the area of the test field (1) under the network (9). The detection side of the test field (1) can be observed through the perforation (13). For this aspect a top view of the underside of the diagnostic test carrier according to FIGS. 2, 4 and 5 is shown in FIG. 3. If analyte is present in the applied sample liquid, the colour of the detection side (6) of the test field (1) will change. A colour forms the intensity of which is a measure of the amount of analyte in the sample liquid.

The invention is further elucidated in more detail by the following examples.

EXAMPLE 1
Production of a Diagnostic Test Carrier According to the Invention A test carrier according to FIG. 2 is produced by the following working steps:

A 5 mm wide double-sided adhesive tape (polyester support and synthetic rubber adhesive) is mounted on a polyester supporting layer containing titanium dioxide. This composite is jointly punched with a 6 mm distance between the holes in order to produce the measuring holes. Afterwards the protective paper of the double-sided adhesive is removed.

A test field composed of 2 film layers is produced as follows:

A. The following components are added together in the following composition to a beaker as pure substances or in the form of stock solutions and admixed by stirring:

| | |
|---|---:|
| Water: | 820.0 g |
| citric acid monohydrate: | 2.5 g |
| calcium chloride dihydrate | 0.5 g |
| sodium hydroxide: | 1.4 g |
| xanthan gum: | 3.4 g |
| tetraethylammonium chloride: | 2.0 g |
| N-octanoyl-N-methyl-glucamide: | 2.1 g |
| polyvinylpyrrolidone (MW 25000): | 3.5 g |
| Transpafill ® (sodium aluminium silicate) | 62.1 g |
| polyvinylpropionate dispersion (50% by weight in water): | 60.8 g |
| bis-(2-hydroxyethyl)-(4-hydroximinocyclohexa-2,5-dienylidine)-ammonium chloride: | 1.2 g |
| 2,18-phosphoromolybdic acid hexasodium salt: | 16.1 g |
| pyrroloquinoline-quinone: | 32 mg |
| glucose dehydrogenase rec. from Acinetobacter calcoaceticus, EC 1.1.99.17: | 1.7 MU (2.4 g) |
| 1-hexanol: | 1.6 g |
| 1-methoxy-2-propanol: | 20.4 g |

The total mass is adjusted with NaOH to a pH of ca. 6 and then applied with an area weight of 89 g/qm onto a 125μ thick polycarbonate foil and dried.

B. The following components are added together in the following composition to a beaker as pure substances or in the form of stock solutions and admixed by stirring:

| | |
|---|---:|
| water: | 579.7 g |
| sodium hydroxide: | 3.4 g |
| Gantrez ® (methyl vinyl ether maleic acid-copolymer): | 13.8 g |
| N-octanoyl-N-methyl-glucamide: | 3.6 g |
| tetraethylammonium chloride: | 9.7 g |
| polyvinylpyrrolidone (MW 25000): | 20.2 g |
| titanium dioxide: | 177.1 g |
| kieselguhr: | 55.3 g |
| polyvinylpropionate dispersion (50% by weight in water): | 70.6 g |
| 2,18-phosphoromolybdic acid hexasodium salt: | 44.3 g |
| potassium hexacyanoferrate (III): | 0.3 g |
| 1-hexanol: | 1.6 g |
| 1-methoxy-2-propanol: | 20.4 g |

The total mass is adjusted with NaOH to a pH of ca. 6 and then applied with an area weight of 104 g/qm onto a polycarbonate foil coated as described in A. and dried.

A 5 mm wide strip of the detection layer produced in this manner is fitted exactly and glued onto the supporting layer with its foil side on the punched double-sided adhesive tape.

Double-sided adhesive tapes as spacers (PVC support and natural rubber adhesive) are glued onto the support foil on both sides of and directly adjoining the detection layer. In the present example one spacer is 6 mm and the other is 9 mm wide. Subsequently the protective foil of the two double-sided adhesive tapes is removed.

A yellow monofilament coarse meshed polyester fabric Scrynel PE 280 HC ("Zürcher Beuteltuchfabrik, Rüschlikon, Switzerland) impregnated with a wetting agent is placed on this compound structure and glued by pressing.

Two single-sided adhesive tapes (PVC support and natural rubber adhesive) are glued onto the yellow net as covers in such a way that the spacers are completely covered and that there is still at least a slight overlap with the reaction zone. This finishes the tape material.

The tape material is cut into 6 mm wide test carriers in such a way that the measuring hole is in the middle of the test carrier.

EXAMPLE 2
Haematocrit Independency of the Test Carriers According to the Invention The test carriers from example 1 can be measured with a reflection photometer. The reflectance values which are a measure of the colour intensity can be converted into glucose concentrations when a calibration curve is available. If the term "relative reflectances" is used they refer to the reflectances on the dry test carrier.

A. Calibration curves are produced by measuring a large number of venous blood samples with different glucose concentrations. The reflectance values and the glucose concentrations of these venous blood samples determined with a reference method can be used to set up a calibration curve.

Figure 6:
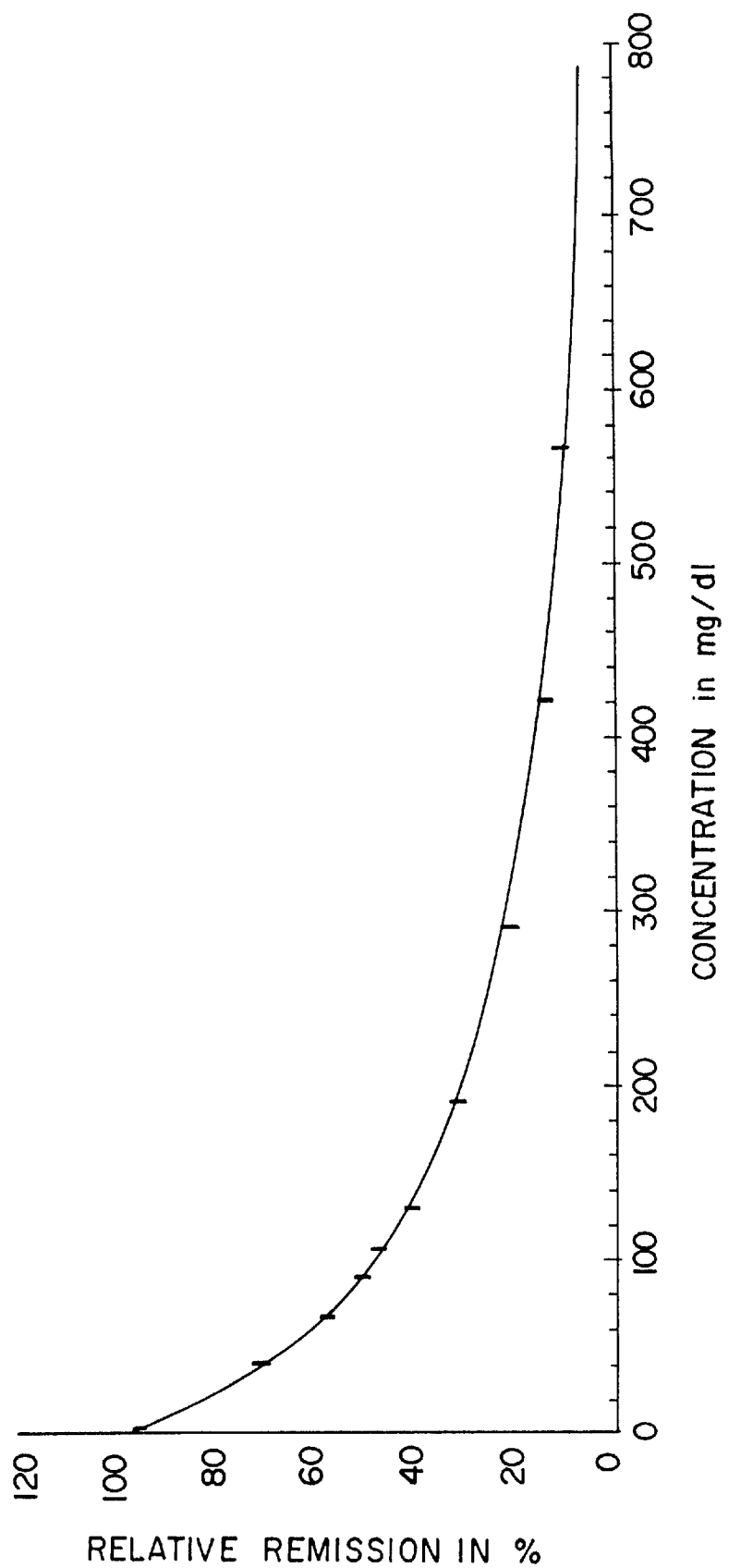
FIGS. 6–9 show calibration curves 1–4 the generation of which is further elucidated in example 2.

In the calibration variant 1 10 μl venous blood was applied to test carriers according to example 1 and the reflectances were measured after 21 sec. The calibration curve 1 (FIG. 6) was determined by a regression calculation from the mean reflectances of 10 test carriers and the reference values of the blood samples.

Figure 7:
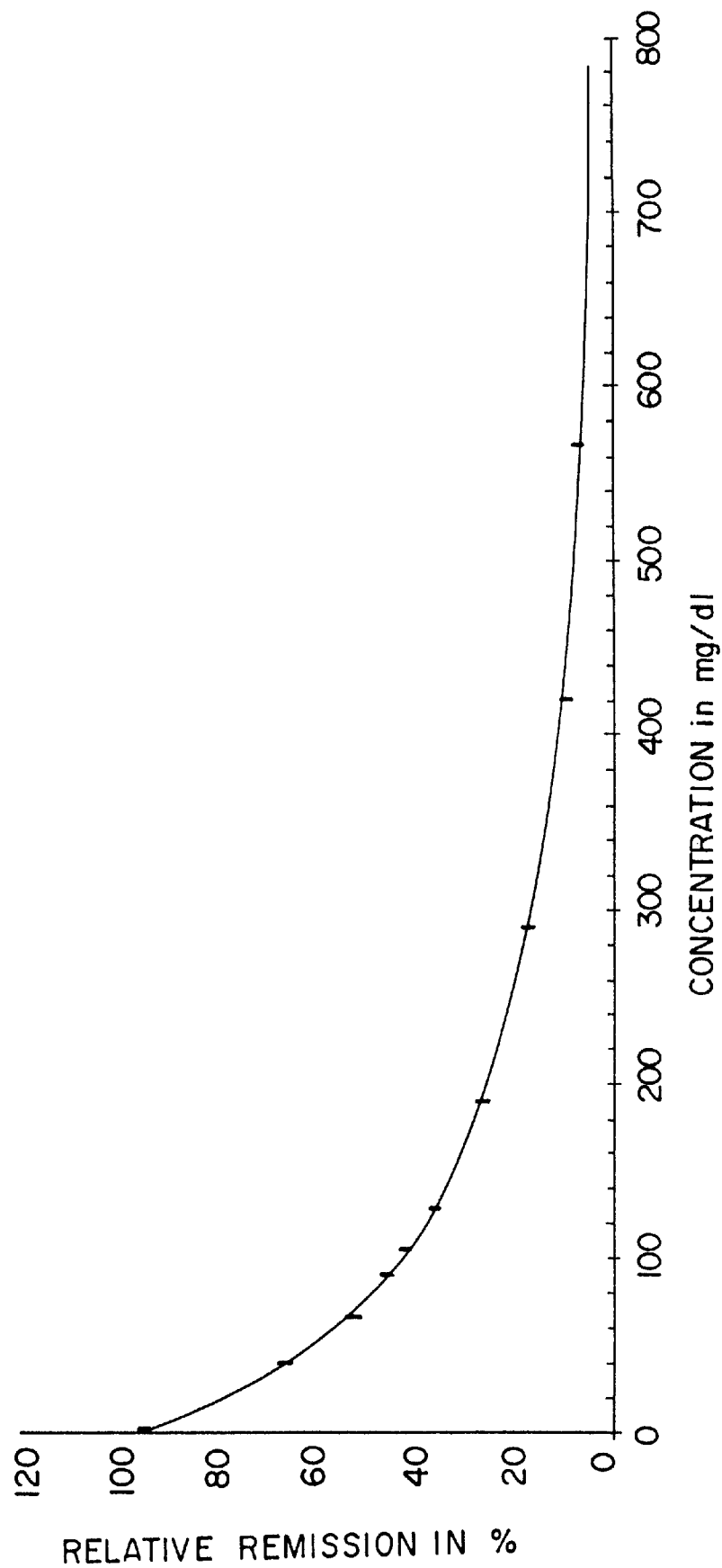

In the calibration variant 2 10 μl venous blood was also applied to test carriers according to example 1 and the reflectances were measured after 30 sec. The calibration curve 2 (FIG. 7) was determined by a regression calculation from the mean reflectances of 10 test carriers and the reference values of the blood samples.

Figure 8:
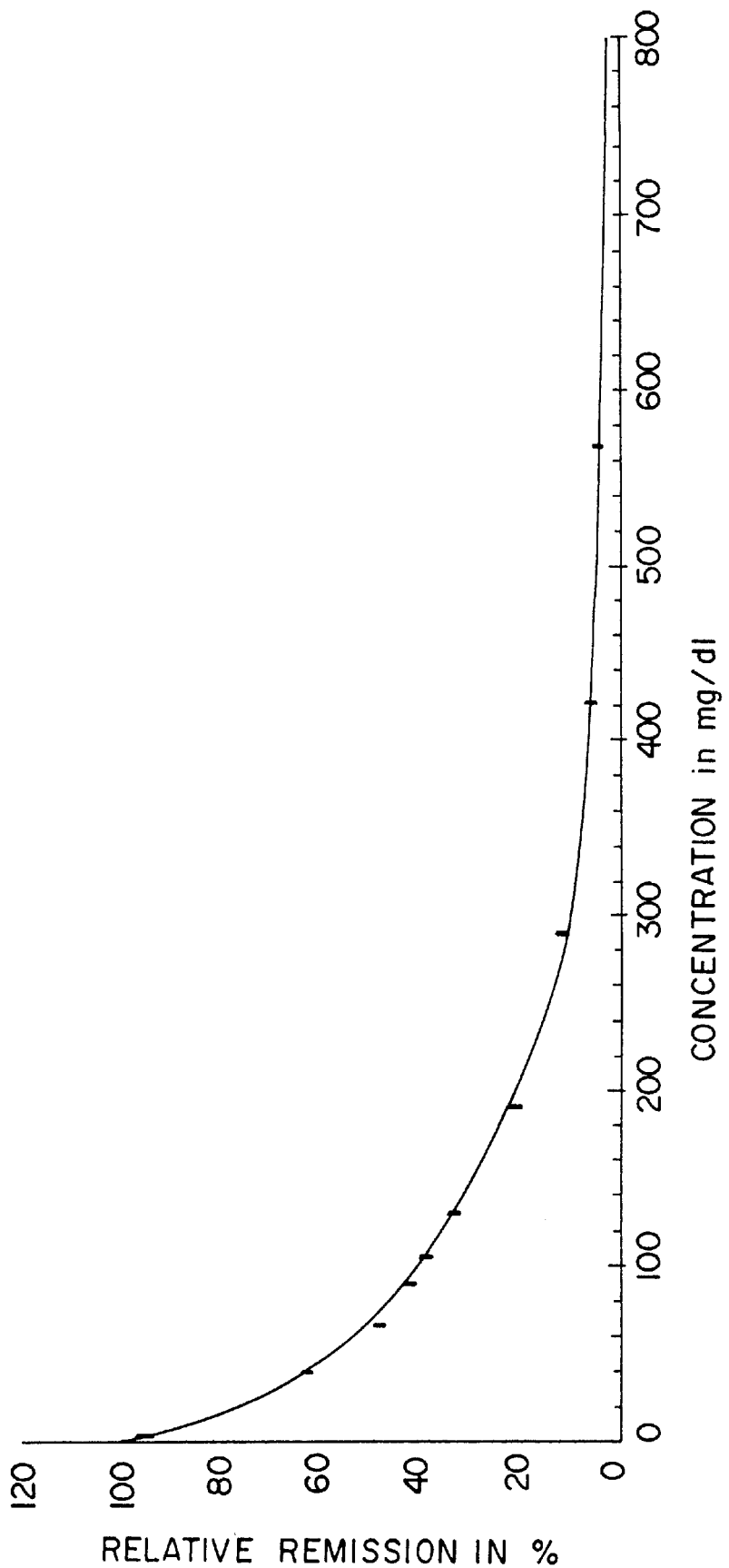

In the calibration variant 3 10 μl venous blood was also applied to test carriers according to example 1 and the reflectances were measured at intervals of 3 sec. As soon as the differences in reflectance were twice successively less than 0.3, the measurement was terminated and the reflectance value was used for the evaluation. The calibration curve 3 (FIG. 8) was determined by a regression calculation from the mean reflectances of 10 test carriers and the reference values of the blood samples.

Figure 9:
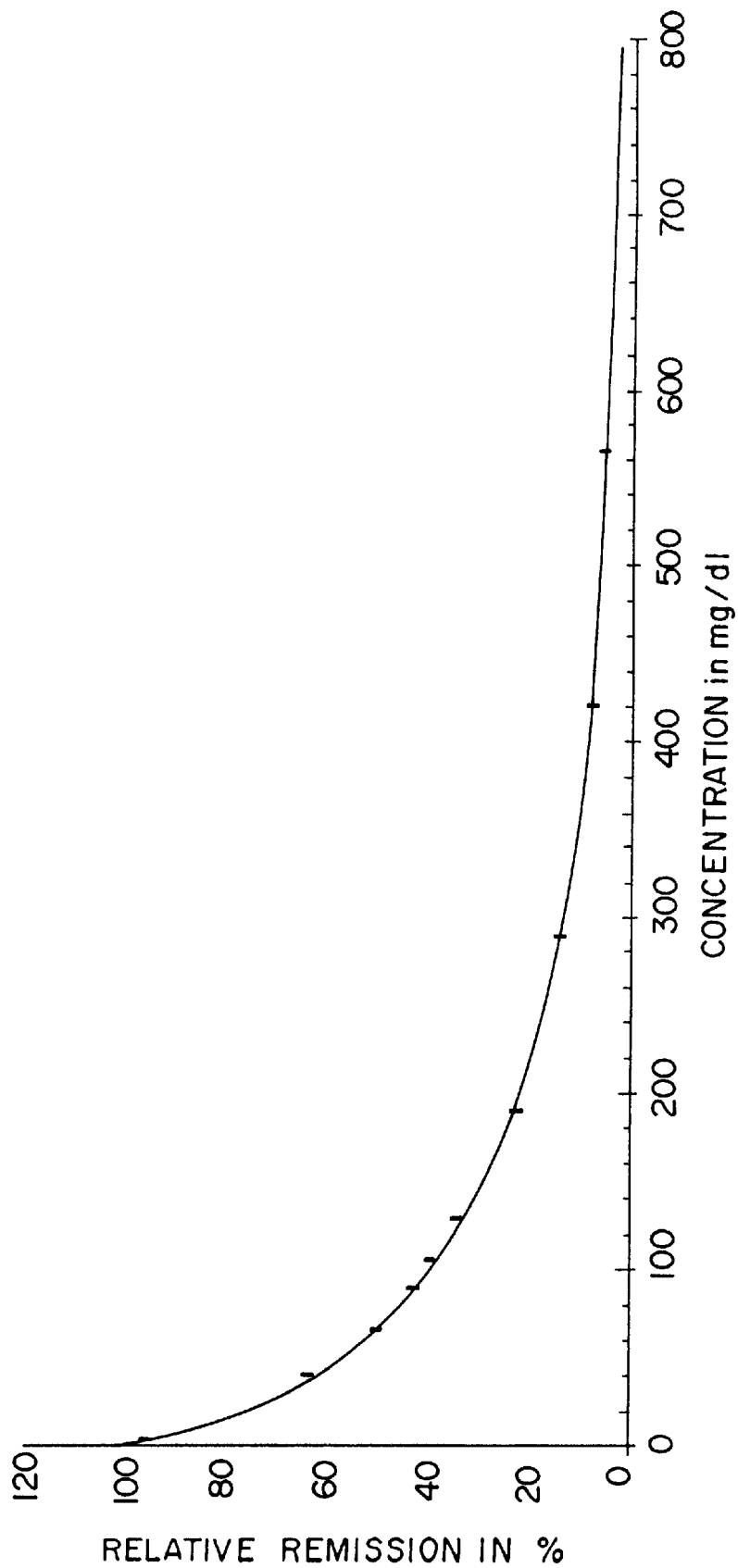

In the calibration variant 4 10 μl venous blood was also applied to test carriers according to example 1 and the reflectances were measured at intervals of 3 sec. As soon as the differences in reflectance were twice successively less than 0.9, the measurement was terminated and the reflectance value was used for the evaluation. The calibration curve 4 (FIG. 9) was determined by a regression calculation from the mean reflectances of 10 test carriers and the reference values of the blood samples.

B. In the case of measurement variant 1, 10 μl venous blood was applied to test carriers according to example 1 and the reflectances were measured after 21 sec. The individual reflectances were converted into glucose concentrations using the corresponding calibration curve according to FIG.

6. The deviation from accuracy was determined from the mean concentrations of 10 test carriers and the reference values of the blood samples and it is shown in Table 1.

In the case of the measurement variant 2, 10 μl venous blood was also applied to test carriers according to example 1 and the reflectances were measured after 30 sec. The individual reflectances were converted into glucose concentrations using the corresponding calibration curve according to FIG. 7. The deviation from accuracy was determined from the mean concentrations of 10 test carriers and the reference values of the blood samples and it is shown in Table 2.

In the case of the measurement variant 3 according to the invention, 10 μl venous blood was also applied to test carriers according to example 1 and the reflectances were measured at intervals of 3 sec. As soon as the differences in reflectance value was used for the successively less than 0.3, the measurement was terminated and the reflectance value was used for the evaluation. The individual reflectances were converted into glucose concentrations using the corresponding calibration curve according to FIG. 8. The deviation from accuracy was determined from the mean concentrations of 10 test carriers and the reference values of the blood samples and it is shown in Table 3.

In the case of the measurement variant 4 according to the invention, 10 μl venous blood was also applied to test carriers according to example 1 and the reflectances were measured at intervals of 3 sec. As soon as the differences in reflectance were twice successively less than 0.9, the measurement was terminated and the reflectance value was used for the evaluation. The individual reflectances were converted into glucose concentrations using the corresponding calibration curve according to FIG. 9. The deviation from accuracy was determined from the mean concentrations of 10 test carriers and the reference values of the blood samples and it is shown in Table 4.

TABLE 1

Haematocrit-dependency of measurement variant 1

| Blood with 30% haematocrit | | | Blood with 57% haematocrit | | |
| --- | --- | --- | --- | --- | --- |
| measured relative reflectance [%] | calculated concentration acc. to calibration curve 1 | deviation from the reference value in % | measured relative reflectance [%] | calculated concentration acc. to calibration curve 1 | deviation from the reference value in % |
| 50.1 | 88.5 | 7.3 | 61.6 | 56.3 | −31.5 |
| 44.2 | 111.0 | 4.9 | 54.3 | 75.3 | −17.1 |
| 37.8 | 143.2 | 3.9 | 45.8 | 104.4 | −20.4 |
| 30.1 | 197.4 | 2.9 | 36.6 | 150.6 | −20.7 |
| 21.1 | 294.7 | 4.6 | 28.3 | 213.8 | −20.5 |

TABLE 2

Haematocrit-dependency of measurement variant 2

| Blood with 30% haematocrit | | | Blood with 57% haematocrit | | |
| --- | --- | --- | --- | --- | --- |
| measured relative reflectance [%] | calculated concentration acc. to calibration curve 2 | deviation from the reference value in % | measured relative reflectance [%] | calculated concentration acc. to calibration curve 2 | deviation from the reference value in % |
| 45.6 | 85.8 | 4.0 | 54.8 | 60.5 | −25.6 |
| 39.7 | 107.6 | 1.6 | 48.3 | 77.6 | −24.5 |
| 33.6 | 137.2 | −0.5 | 39.0 | 110.4 | −15.8 |
| 25.4 | 193.4 | 0.9 | 30.0 | 159.1 | −16.2 |
| 16.3 | 295.9 | 5.0 | 22.0 | 226.3 | −15.9 |

TABLE 3

Compensation of haematocrit dependency by measurement variant 3 according to the invention

| Blood with 30% haematocrit | | | Blood with 57% haematocrit | | |
| --- | --- | --- | --- | --- | --- |
| measured relative reflectance [%] | calculated concentration acc. to calibration curve 3 | deviation from the reference value in % | measured relative reflectance [%] | calculated concentration acc. to calibration curve 3 | deviation from the reference value in % |
| 43.0 | 82.3 | −0.2 | 46.7 | 72.4 | 1.0 |
| 37.5 | 102.6 | −3.0 | 40.6 | 91.4 | 0.6 |
| 30.6 | 134.1 | −2.7 | 29.6 | 139.4 | 6.2 |
| 10.8 | 274.6 | −2.5 | 11.7 | 265.8 | −1.2 |

TABLE 4

Compensation of haematocrit dependency by measurement variant 4 according to the invention

| Blood with 30% haematocrit | | | Blood with 57% haematocrit | | |
|---|---|---|---|---|---|
| measured relative reflectance [%] | calculated concentration acc. to calibration curve 4 | deviation from the reference value in % | measured relative reflectance [%] | calculated concentration acc. to calibration curve 4 | deviation from the reference value in % |
| 44.2 | 84.1 | 1.9 | 48.8 | 70.3 | −2.0 |
| 38.6 | 104.6 | −1.2 | 42.8 | 88.8 | −2.2 |
| 32.2 | 133.6 | −3.1 | 33.3 | 128.1 | −2.4 |
| 22.6 | 195.5 | 2.0 | 22.8 | 194.3 | 2.3 |
| 13.5 | 296.4 | 5.2 | 15.4 | 269.7 | 0.3 |

In the case of 20 haematocrit measurement variants 3 and 4 result in similarly small deviations to 30% haematocrit.

What is claimed is:

1. A diagnostic test carrier for the determination of an analyte from a whole blood sample, comprising
   a reagent system; and
   a test field, containing said reagent system, wherein the test field has a sample application side onto which a whole blood sample is applied, and a detection side which produces an optically detectable signal when the analyte reacts with the reagent system;
   wherein the test field comprises a transparent foil, a first film layer applied to the top of the foil and a second film layer applied to the top of the first film layer so that the two film layers are fixedly attached one over the other in direct intimate contact with each other;
   wherein the transparent foil has a foil side and a non-foil side, and the foil side is the detection side of the test field and the first film layer is applied to the non-foil side;
   wherein when in a wet state the first film layer scatters light less than the second film layer scatters light;
   wherein the test field is constructed such that erythrocytes present in the sample substantially do not reach the detection side of the test field; and
   wherein the first film layer and second film layer are formed from (a) a dispersion of a polymeric film former which contains the polymeric film former and a swelling agent in a homogeneous dispersion, or (b) an emulsion of a polymeric film former which contains the polymeric film former and a swelling agent in a homogeneous emulsion, wherein the swelling capability of the swelling agent is at a level which allows the optically detectable change to be measured on the detection side after a maximum of one minute.

2. The diagnostic test carrier according to claim 1, wherein when in a dry state the thickness of the first film layer and the second film layer together are a maximum of 0.08 mm.

3. The diagnostic test carrier according to claim 1, wherein the reagent system is located in the first film layer.

4. The diagnostic test carrier according to claim 1, wherein the reagent system is located in both the first film layer and the second film layer.

5. The diagnostic test carrier according to claim 1, wherein the transparent foil is polycarbonate foil.

6. The diagnostic test carrier according to claim 1, wherein the first film layer contains no fillers.

7. The diagnostic test carrier according to claim 1, wherein the first film layer contains fillers whose refractive index is about the refractive index of water.

8. The diagnostic test carrier according to claim 1, wherein the second layer contains a pigment with a refractive index of at least 2.5.

9. The diagnostic test carrier according to claim 1, wherein the first film layer has a pigment of sodium aluminum silicate and the second film layer has a pigment of titanium dioxide.

10. The diagnostic test carrier according to claim 1, wherein the detectable signal is a color change signal.

11. The diagnostic test carrier of claim 1 wherein the first and second film layers are produced from coating compounds containing the same polymeric film formers.

12. The diagnostic test carrier of claim 1 wherein the first and second film layers are produced from coating compounds containing different polymeric film formers.

13. The diagnostic test carrier according to claim 1, wherein when in a dry state the thickness of the first film layer and the second film layer together are a maximum of 0.20 mm.

14. The diagnostic test carrier according to claim 13, wherein the second film layer is about two times to about five times thicker than the first film layer.

15. The diagnostic test carrier according to claim 1, wherein the first film layer and the second film layer contain a non-haemolyzing wetting agent.

16. The diagnostic test carrier according to claim 15, wherein the wetting agent of at least one film layer is N-octanoyl-N-methyl-glucamide.

17. A diagnostic test carrier for the determination of an analyte from a whole blood sample, comprising
   a test field having a reagent system therein, wherein the test field has a sample application side onto which a whole blood sample is applied, and a detection side which produces an optically detectable signal when the analyte reacts with the reagent system, wherein the test field is constructed such that erythrocytes present in the sample do not reach the detection side of the test field, and wherein the test field comprises a transparent foil, a first film layer applied to the top of the foil and a second film layer applied to the top of the first film layer so that the two film layers are fixedly attached one over the other in direct intimate contact with each other, wherein the first film layer and the second film layer are both formed from (a) a dispersion of a polymeric film former which contains the polymeric film former and a swelling agent in a homogeneous dispersion, or (b) an emulsion of a polymeric film former which contains the polymeric film former and a swelling agent in a homogeneous emulsion, wherein the swelling capability of the swelling agent is at a level which allows the optically detectable change to be measured on the detection side after a maximum of one minute, wherein the transparent foil has a foil side and a non-foil side, and the foil side comprises the detection side of the test field, wherein the first film layer is applied to the non-foil side, and wherein the first film layer scatters light less in a wet state than the second film layer scatters light;

a supporting layer to which the detection side of the test field is attached;

a network which covers the sample application side of the test field, extends beyond the test field, and is attached to the supporting layer beyond the test field by means of spacers; and a cover arranged over the areas of the network which extend beyond the test field and slightly cover the area of the test field on each side in such a way that a sample application site is substantially not covered by the cover in the region of the network that covers the test field;

wherein the network defines a capillary gap between the cover and the test field and the cover and the supporting layer, such that capillary liquid transport is possible for the removal of excess sample when the test field is saturated with liquid.

18. The diagnostic test carrier according to claim 17, wherein the detectable signal is a color change signal.

19. The diagnostic test carrier according to claim 17, wherein the spacers are about the same thickness as the test field.

20. The diagnostic test carrier according to claim 17, wherein the detection side of the test field is visible through the supporting layer.

21. The diagnostic test carrier according to claim 20, wherein the supporting layer is transparent such that the detection side of the test field is visible therethrough.

22. The diagnostic test carrier according to claim 20, wherein the supporting layer has at least one hole in the area of the detection layer, through which the detection layer is visible, and wherein the hole is smaller than the detection layer such that the detection layer contacts at least a portion of an area of the supporting layer surrounding the hole.

23. The diagnostic test carrier according to claim 17, wherein the network is a coarse, meshed, monofilament fabric.

24. The diagnostic test carrier according to claim 23, wherein the network is polyester.

25. The diagnostic test carrier according to claim 17, wherein the network is essentially non-absorptive and essentially does not allow capillary liquid transport, such that the greatest possible amount of blood is available for the test field.

26. The diagnostic test carrier according to claim 17, wherein the thickness of the network is such that if the test field becomes saturated, excess liquid is transported over the saturated test field and the filled meshes of the network by capillary force into the area of the network under the cover and away from the sample application site.

27. The diagnostic test carrier according to claim 26, wherein the thickness of the network is between 50 and 400 μm.

* * * * *